United States Patent
Müller et al.

(12)

(10) Patent No.: US 6,255,528 B1
(45) Date of Patent: Jul. 3, 2001

(54) PROCESS FOR PREPARING PHENETHYLAMINES AND NOVEL CHEMICAL COMPOUNDS

(76) Inventors: Peter Müller, Lütticher Str. 64, 50674 Köln; Albrecht Marhold, Carl-Duisberg-Str. 329, 51373 Leverkusen, both of (DE)

( * ) Notice: Subject to any disclaimer, the term of this patent is extended or adjusted under 35 U.S.C. 154(b) by 0 days.

(21) Appl. No.: 09/608,927

(22) Filed: Jul. 3, 2000

(30) Foreign Application Priority Data

Jul. 6, 1999 (DE) ............................................. 199 31 116

(51) Int. Cl.⁷ ..................................................... C07C 213/00
(52) U.S. Cl. .......................... 564/347; 564/374; 549/366; 549/440; 549/467
(58) Field of Search ..................................... 564/383, 347, 564/374; 549/380, 455, 504, 366, 440, 467

(56) References Cited

PUBLICATIONS

J. Am. Chem. Soc. 63, (month unavailable) 1941, Suter et al, Some Fluorinated Amines of the Presser Type, pp. 602–605.

J. Org. Chem., 23, Dec. 1958, pp. 1979–1984, Benington et al, Psychopharmacological Activity of Ring– and Side Chain–Substituted β–Phenethylamines.

*Primary Examiner*—Samuel Barts
(74) *Attorney, Agent, or Firm*—Joseph C. Gil; Diderico van Eyl

(57) ABSTRACT

Fluorine-containing phenethylamines are obtained in an advantageous manner by reacting fluorine-containing bromobenzenes with acrylamide in the presence of a palladium catalyst, hydrogenating the resulting arylacrylamides catalytically and then rearranging the arylamides obtained. The invention also embraces novel arylacrylamides and novel arylamides.

10 Claims, No Drawings

PROCESS FOR PREPARING PHENETHYLAMINES AND NOVEL CHEMICAL COMPOUNDS

The present invention relates to a novel process for preparing fluorine-containing phenethylamines and to the resulting novel chemical compounds.

BACKGROUND OF THE INVENTION 4-fluorophenethylamine, 4-(trifluoromethoxy)-phenethylamine and other fluorine-containing phenethylamines are intermediates for preparing agrochemicals. J. Am. Chem. Soc. 63, 602 (1941) discloses that 4-fluorophenethylamine can be prepared in a multi-step process. This process gives, starting from p-fluorophenylmagnesium bromide, by addition of ethylene oxide with subsequent hydrolysis, p-fluorophenethyl alcohol which is converted with phosphorus tribromide into p-fluoro. Disadvantageous for using this process on an industrial scale are the high expenditure required for carrying out a Grignard reaction and the multi-step synthesis.

In another process for preparing 4-fluorophenethylamine (see J. Org. Chem. 23, 1979 (1958)), p-fluorobenzylchloride is used as starting material, which is reacted with sodium cyanide to give p-fluorophenylacetonitrile which is then finally reduced using sodium aluminium hydride or lithium aluminium hydride. This process has the disadvantages that some of the required benzyl chlorides are difficult to prepare, and that the handling of sodium aluminium hydride or lithium aluminium hydride requires great safety precautions. Thus, this process is likewise unsuitable for industrial application.

There is therefore still a demand for a process which allows the preparation of fluorine-containing phenethylamines in a simple manner, from easily obtainable starting materials and without any high technical expenditure.

SUMMARY OF THE INVENTION

The present invention, accordingly, provides a process for preparing fluorine-containing phenethylamines of the Formula (I)

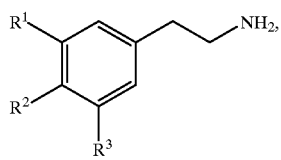

(I)

in which
one of the radicals $R^1$ and $R^2$ represents fluorine, trifluoromethyl, trifluoromethoxy, tetrafluoroethoxy or pentafluoroethoxy and the other represents hydrogen, $C_1$-$C_6$-alkyl, $C_1$-$C_6$-alkoxy, fluorine, trifluoromethyl, trifluoromethoxy, tetrafluoroethoxy or pentafluoroethoxy or
$R^1$ and $R^2$ together represent —O—$CF_2$—O—, —O—$CF_2$—$CF_2$— or —O—$CF_2$—$CF_2$—O— and
$R^3$ represents hydrogen, chlorine, $C_1$-$C_6$-alkyl or $C_1$-$C_6$-alkoxy, in which in a first step a substituted bromobenzene of the Formula

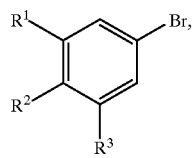

(II)

in which
$R^1$, $R^2$ and $R^3$ are as defined under Formula (I)
is reacted with acrylamide in the presence of a palladium catalyst,
in a second step the resulting arylacrylamide of the Formula

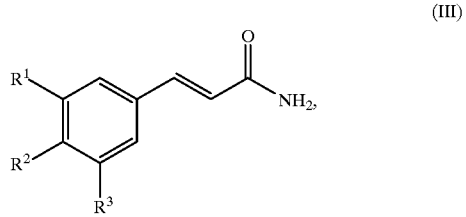

(III)

in which
the radicals $R^1$, $R^2$ and $R^3$ are as defined under Formula (I)
is hydrogenated catalytically and
in a third step the arylamide obtained in step two of the Formula

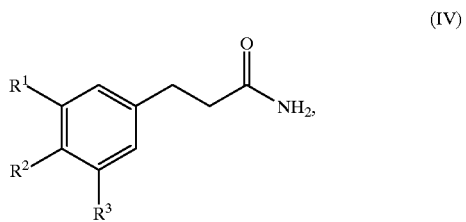

(IV)

in which
$R^1$, $R^2$ and $R^3$ are as defined under Formula (I)
is rearranged.

The present invention furthermore relates to arylacrylamides of the Formula

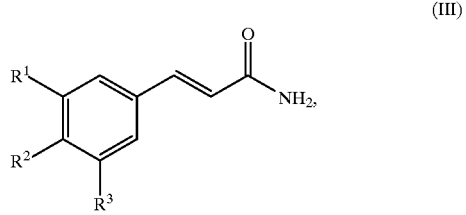

(III)

in which
one of the radicals $R^1$ and $R^2$ represents fluorine, trifluoromethyl, trifluoromethoxy, tetrafluoroethoxy or pentafluoroethoxy and the other represents hydrogen, $C_1$-$C_6$-alkyl, $C_1$-$C_6$-alkoxy, fluorine, trifluoromethyl, trifluoromethoxy, tetrafluoroethoxy or pentafluoroethoxy or
$R^1$ and $R^2$ together represent —O—$CF_2$—O—, —O—$CF_2$—$CF_2$— or —O—$CF_2$—$CF_2$—O— and
$R^3$ represents hydrogen, chlorine, $C_1$-$C_6$-alkyl or $C_1$-$C_6$-alkoxy, except for the compounds 3-(3-fluorophenyl)-acrylamide, 3-[3-(trifluoromethyl)-phenyl]-acrylamide and 3-[4-(trifluoromethyl)-phenyl]-acrylamide.

The present invention also relates to arylamides of the Formula

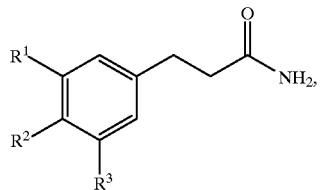

(IV)

in which one of the radicals $R^1$ and $R^2$ represents fluorine, trifluoromethyl, trifluoromethoxy, tetrafluoroethoxy or pentafluoroethoxy and the other represents hydrogen, $C_1$–$C_6$-alkyl, $C_1$–$C_6$-alkoxy, fluorine, trifluoromethyl, trifluoromethoxy, tetrafluoroethoxy or pentafluoroethoxy or $R^1$ and $R^2$ together represent —O—$CF_2$—O—, —O—$CF_2$—$CF_2$— or —O—$CF_2$—$CF_2$—O— and $R^3$ represents hydrogen, chlorine, $C_1$–$C_6$-alkyl or $C_1$–$C_6$-alkoxy, except for the compounds 3-(3-fluorophenyl)-acrylamide, 3-(4-fluorophenyl)-acrylamide, 3-[3-(trifluoromethyl)-phenyl]-acrylamide and 3-[4-(trifluoromethyl)-phenyl]-acrylamide.

DETAILED DESCRIPTION OF THE INVENTION

In the Formulae (I), (II), (III) and (IV), one of the radicals $R^1$ and $R^2$ preferably represents a radical from the group consisting of fluorine, trifluoromethyl, trifluoromethoxy, tetrafluoroethoxy and pentafluoroethoxy, and the other radical preferably represents hydrogen, or $R^1$ and $R^2$ together preferably represent —O—$CF_2$—O—, —O—$CF_2$—$CF_2$— or —O—$CF_2$—$CF_2$—O—. $R^3$ preferably represents hydrogen or chlorine.

In the Formulae (I), (II), (III) and (IV), $R^1$ and $R^3$ particularly preferably represent hydrogen and $R^2$ represents fluorine, trifluoromethyl or trifluoromethoxy, or $R^1$ represents fluorine, trifluoromethyl or trifluoromethoxy and $R^2$ and $R^3$ represent hydrogen or $R^1$ and $R^2$ together represent —O—$CF_2$—O—, —O—$CF_2$—$CF_2$— or —O—$CF_2$—$CF_2$—O— and $R^3$ represents hydrogen.

Tetrafluoroethoxy radicals are preferably 1,1,2,2-tetrafluoroethoxy radicals.

According to the invention, the fluorine-containing phenethylamines listed in Table 1 are very particularly preferably prepared.

TABLE 1

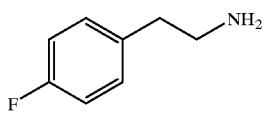

TABLE 1-continued

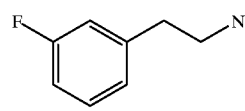

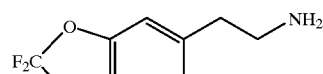

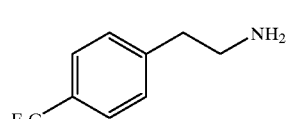

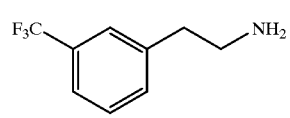

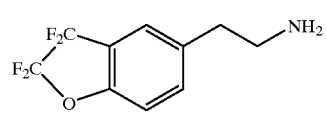

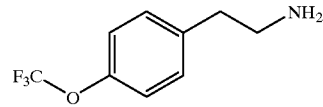

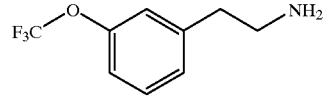

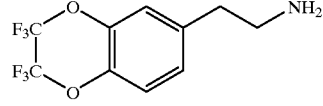

The reaction of the bromobenzenes of the Formula (II) with acrylamide to give arylacrylamides of the Formula (III) is carried out in the presence of a palladium catalyst, preferably in the presence of a diluent and a reaction auxiliary.

The bromobenzenes of the Formula (II) are either commercially available, or they can be prepared by processes known per se or analogously to these processes.

Suitable palladium catalysts for the first reaction step are, for example, palladium complexes having aryl- or alkylphosphines as ligands. It is possible, for example, to add both the complexes themselves and palladium(II) salts and the free ligands separately.

Suitable diluents for the first reaction step are dipolar aprotic solvents and mixtures comprising these, for example with aliphatic and/or aromatic hydrocarbons or ethers. Examples of dipolar aprotic solvents are: nitriles, such as acetonitrile, propionitrile, n- and i-butyronitrile and benzonitrile, amides, such as formamide, N-methylformamide, N,N-dimethylformamide, N,N-dimethylacetamide and N-methylpyrrolidone, esters, such as methyl acetate, ethyl acetate and butyl acetate, sulphones, such as sulpholane. It is also possible to use mixtures of dipolar aprotic solvents.

Suitable reaction auxiliaries for the first reaction step are, for example, weak inorganic or organic bases. Preference is given to alkaline earth metal and alkali metal acetates, carbonates and bicarbonates, such as sodium acetate, potassium acetate, calcium acetate and ammonium acetate, sodium carbonate, potassium carbonate and ammonium carbonate, sodium bicarbonate and potassium bicarbonate, and to tertiary amines, such as trimethylamine, triethylamine and tributylamine. Preference is given to using sodium acetate or potassium acetate.

For carrying out the first reaction step, it is possible to use, for example, the bromobenzene of the Formula (II) in question and acrylamide in amounts of from 0.5 to 2 mol of the bromobenzene in question, based on 1 mol of acrylamide. This amount is preferably from 0.9 to 1.1 mol. Particular preference is given to using equimolar amounts of the bromobenzene of the Formula (II) in question and acrylamide. Based on the bromobenzene in question, it is possible to use, for example, from 0.005 to 20 mmol, preferably from 0.1 to 10 mmol, of palladium catalyst and from 1 to 10 equivalents, preferably from 1 to 3 equivalents, of reaction auxiliary. If a palladium(II) salt and free phosphine ligands are employed separately, the molar ratio of palladium(II) salt to phosphine ligands can be, for example, from 1:1 to 1:10, preferably from 1:2 to 1:4. The amount of diluent is not critical. Preference is given to using from 100 to 2000 ml per mole of the bromobenzene of the Formula (II) in question.

The reaction temperature in the first process step can be varied within a relatively wide range. It can be, for example, between 50 and 180° C., preferably between 80 and 150° C.

The catalytic hydrogenation of arylacrylamides of the Formula (III) to give arylamides of the Formula (IV) is generally carried out using hydrogen gas, preferably in the presence of a diluent.

Suitable catalysts for carrying out this hydrogenation are, for example, noble metals on support materials, in particular palladium and platinum on carbon, silicates, silica, alumina, zeolites, barium sulphate, calcium carbonate and spinelles. Particular preference is given to palladium on carbon. Based on the finished catalyst, the catalyst may comprise, for example, from 0.1 to 20% by weight of noble metal. This amount is preferably from 5 to 15% by weight.

Suitable diluents for the second reaction step are water, organic solvents and any mixtures thereof. Examples of organic solvents which may be mentioned are: aliphatic, alicyclic and aromatic hydrocarbons, such as petroleum ether, hexane, heptane, cyclohexane, methylcyclohexane, benzene, toluene, xylene and decaline, ethers, such as diethyl ether, diisopropyl ether, methyl-t-butyl ether and methyl-t-amyl ether, dioxane, tetrahydrofuran, 1,2-dimethoxyethane, 1,2-diethoxyethane, diethylene glycol dimethyl ether and anisol, esters, such as methyl acetate, ethyl acetate or butyl acetate, and alcohols, such as methanol, ethanol, n- and 1-propanol, n-, i-, s- and t-butanol, ethanediol, propane-1,2-diol, ethoxyethanol, methoxyethanol, diethylene glycol monomethyl ether and diethylene glycol monoethyl ether. Preferred solvents are tetrahydrofuran, toluene, ethyl acetate, methyl-t-butyl ether and ethanol. Particular preference is given to using tetrahydrofuran.

When carrying out the second reaction step, it is possible to use, for example, from 0.001 to 0.5 mol, preferably from 0.05 to 0.2 mol, of catalyst (calculated as metal) and from 1 to 10 l of diluent per mole of arylacrylamide of the Formula (III). The catalyst can be used for several successive reactions. In the case of batches where the catalyst used has already been used before, the reaction time may be prolonged. This can be compensated for by adding fresh catalyst, for example in an amount of from 5 to 25% by weight, based on the total of the catalyst employed.

The reaction temperature for the second reaction step can be varied within a relatively wide range. It can be, for example, between 0 and 120° C., preferably between 20 and 70° C. The hydrogen pressure can be, for example, from 1 to 100 bar, and is preferably between 5 and 20 bar.

The rearrangement of the arylamides of the Formula (IV) to the phenethylamines of the Formula (I) can, for example, be carried out using an aqueous base in the presence of bromine or chlorine. Suitable bases are, for example, aqueous alkali metal hydroxides. Preference is given to using aqueous solutions of sodium hydroxide or potassium hydroxide.

Per mole of arylamide of the Formula (IV), it is possible to employ, for example, from 1 to 20 equivalents of aqueous alkali metal hydroxide and from 0.5 to 5 equivalents of bromine or chlorine. Preference is given to using from 4 to 8 equivalents of alkali metal hydroxide and from 0.9 to 1.5 equivalents of bromine or chlorine.

The temperature of the rearrangement can be varied within wide limits. The upper limit of the temperature is given by the boiling point of the reaction mixture. The reaction is preferably carried out at from 50 to 120° C.

The reactions of the first and the third step of the process according to the invention can be carried out under atmospheric pressure or elevated pressure. The reactions are preferably carried out under atmospheric pressure.

The practice of the reactions and the work-up and isolation of the reaction products can be carried out by generally customary known methods. The end products are preferably purified by crystallization, distillation or by removing the volatile components, if appropriate under reduced pressure.

With respect to the arylacrylamides of the present invention the preferred and particularly preferred meanings of the radicals $R^1$, $R^2$ and $R^3$ are as defined above.

With respect to the arylamides of the present invention the preferred and particularly preferred meanings of the radicals $R^1$, $R^2$ and $R^3$ are as defined above.

The novel arylacrylamides and arylamides can be prepared as described above and be used as intermediates, an intermediate isolation of which is not always required, for preparing fluorine-containing phenethylamines of the Formula (I). Intermediate isolation may be dispensed with in particular at the stage of the acrylamides of the Formula (IV).

The process according to the invention allows the preparation of fluorine-containing phenethylamines in a three-step process, providing a process which can be carried out in a simple manner even on an industrial scale, thus opening up a considerably more favourable route to fluorine-containing phenethylamines. Particular safety precautions are not required.

The discovery of the arylacrylamides according to the invention and the arylamides according to the invention was only possible through the conception of the process according to the invention of the scope shown here.

EXAMPLES

Example 1

275 ml of dry dimethylformamide were flushed with nitrogen for 1 hour. 100 g of 1-bromo-4-(trifluoromethoxy)- benzene, 29.4 g of acrylamide, 101 mg of palladium(II) acetate, 216 mg of triphenylphosphine and 67.8 g of sodium acetate were then added successively, and the mixture was stirred at 130° C. for 20 hours. After cooling, the mixture was filtered, the filtrate was concentrated, the filter residue was combined with the concentrated filtrate and the mixture was suspended in 200 ml of water and filtered again. The resulting filter residue was washed with 200 ml of n-hexane and air-dried. This gave 84 g of 3-[4-(trifluoromethoxy)-phenyl]-acrylamide. According to GC, stated in area percent, the product was 95.9% pure. This corresponds to a yield of 83% of theory.

Example 2

In a stirred autoclave, 250 g of the 3-[4-(trifluoromethoxy)-phenyl]-acrylamide obtained according to Example 1 were initially charged dissolved in 1250 ml of tetrahydrofuran, 6.2 g of palladium-on-carbon (10% by weight) were added, and the acrylamide was hydrogenated at 50° C. and a hydrogen pressure between 5 and 10 bar until the reaction had gone to completion (3 hours). The catalyst was then filtered off and the solvent removed by distillation. This gave 221 g of 3-[4-(trifluoromethoxy)-phenyl]-propionamide. According to GC, stated in area percent, the product was 98.1% pure. This corresponds to a yield of 86% of theory.

Example 3

21.1 g of sodium hydroxide were initially charged in 70 ml of water, and 15 g of bromine were added dropwise at room temperature. After the addition had ended, 20 g of the 3-[4-(trifluoromethoxy)-phenyl]-propionamide obtained according to Example 2 were added. The mixture was then heated under reflux for 3 hours. After cooling, the reaction mixture was diluted with 200 ml of water and extracted three times with in each case 75 ml of methyl-t-butyl ether. The combined organic phases were dried over magnesium sulphate, filtered and concentrated. The residue was distilled under reduced pressure over a short Vigreux column. This gave 10.3 g of 2-[4-(trifluoromethoxy)-phenyl]-ethylamine, which distilled over at from 83 to 86° C. and 11 mbar. According to GC, stated in area percent, the product was 99% pure. This corresponds to a yield of 58% of theory.

Example 4

20 g of the 3-[4-(trifluoromethoxy)-phenyl]-propionamide obtained according to Example 2 were initially charged in 30 ml of water. At 60° C., a mixture of 21.1 g of sodium hydroxide, 50 ml of water and 15 g of bromine was added dropwise to this suspension. The mixture was then heated under reflux for 3 hours. The reaction mixture was diluted with 200 ml of water and then worked up and purified as described in Example 3. This gave 8.8 g of 3-[4-(trifluoromethoxy)-phenyl]-acrylamide which distilled over at from 84 to 87° C. and 11 mbar. According to GC, stated in area percent, the product was 99% pure. This corresponds to a yield of 49% of theory.

Example 5

21.1 g of sodium hydroxide and 20 g of 3-[4-(trifluoromethoxy)-phenyl]-propionamide, prepared according to Example 2, were initially charged in 70 ml of water, and 15 g of bromine were added dropwise at room temperature. The mixture was then heated under reflux for 3 hours. The reaction mixture was subsequently admixed with 200 ml of water and worked up and purified as described in Example 3. This gave 12.9 g of 2-[4-(trifluoromethoxy)-phenyl]-ethylamine which distilled over at from 84 to 86° C. and 10 mbar. According to GC, stated in area percent, the resulting product was 99% pure. This corresponds to a yield of 72% of theory.

What is claimed is:

1. A process for preparing fluorine-containing phenethylamines of the Formula

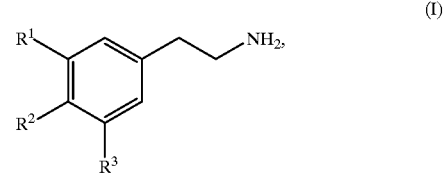

in which one of the radicals $R^1$ and $R^2$ represents fluorine, trifluoromethyl, trifluoromethoxy, tetrafluoroethoxy or pentafluoroethoxy and the other represents hydrogen, $C_1$–$C_6$-alkyl, $C_1$–$C_6$-alkoxy, fluorine, trifluoromethyl, trifluoromethoxy, tetrafluoroethoxy or pentafluoroethoxy or $R^1$ and $R^2$ together represent —O—$CF_2$—O—, —O—$CF_2$—$CF_2$— or —O—$CF_2$—$CF_2$—O— and $R^3$ represents hydrogen, chlorine, $C_1$–$C_6$-alkyl or $C_1$–$C_6$-alkoxy, which comprises in a first step reacting a substituted bromobenzene of the Formula

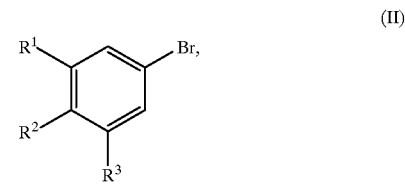

in which $R^1$, $R^2$ and $R^3$ are as defined under Formula (I)

with acrylamide in the presence of a palladium catalyst, in a second step hydrogenating catalytically the resulting arylacrylamide of the Formula

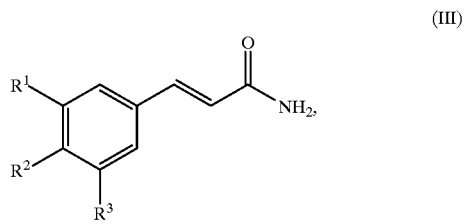

in which the radicals $R^1$, $R^2$ and $R^3$ are as defined under Formula (I) and in a third step rearranging the arylamide obtained in step two of the Formula

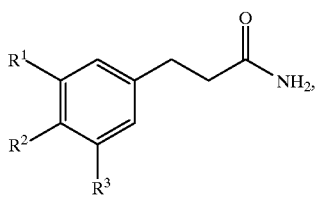

in which

R¹, R² and R³ are as defined under Formula (I).

2. The process of claim 1, in which in the Formulae (I), (II), (III) and (IV) one of the radicals R¹ and R² represents a radical from the group consisting of fluorine, trifluoromethyl, trifluoromethoxy, tetrafluoroethoxy and pentafluoroethoxy and the other radical represents hydrogen or R¹ and R² together represent —O—CF₂—O—, —O—CF₂—CF₂— or —O—CF₂—CF₂—O— and R³ represents hydrogen or chlorine.

3. The process of claim 1, in which the palladium catalysts used for the first reaction step are palladium complexes having aryl- or alkylphosphines as ligands.

4. The process of claim 1, using in the first reaction step from 0.5 to 2 mol of the bromobenzene in question, based on 1 mol of acrylamide, and from 0.005 to 20 mmol of palladium catalyst, based on the bromobenzene in question are used, and that this process step is carried out at from 50 to 180° C.

5. The process of claim 1, in which the first reaction step is carried out at from 50 to 180° C.

6. The process claim 1, in which the catalytic hydrogenation of arylacrylamides of the Formula (III) is carried out using hydrogen gas and noble metals on support materials as catalyst.

7. The process of claim 1, in which the second reaction step is carried out in the presence of a diluent.

8. The process of claim 1 in which in the second reaction step, from 0.001 to 0.5 mol of catalyst (calculated as metal) are used per mole of arylacrylamide of the Formula (III).

9. The process of claim 1, in which the second reaction step is carried out from 0 to 120° C.

10. The process of claim 1, in which the rearrangement of the arylamides of the Formula (IV) to the phenethylamines of the Formula (I) is carried out using an aqueous base in the presence of bromine or chlorine.

* * * * *